(12) United States Patent
Hirano et al.

(10) Patent No.: US 6,686,508 B2
(45) Date of Patent: Feb. 3, 2004

(54) PROCESS FOR PRODUCING BISPHENOL A

(75) Inventors: Kazuyuki Hirano, Chiba (JP); Ken Fujimoto, Chiba (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/258,578

(22) PCT Filed: Feb. 21, 2002

(86) PCT No.: PCT/JP02/01535
§ 371 (c)(1),
(2), (4) Date: Oct. 31, 2002

(87) PCT Pub. No.: WO02/070444
PCT Pub. Date: Sep. 12, 2002

(65) Prior Publication Data
US 2003/0120120 A1 Jun. 26, 2003

(30) Foreign Application Priority Data
Mar. 5, 2001 (JP) .................................... 2001-060201

(51) Int. Cl.⁷ .............................................. C07C 39/16
(52) U.S. Cl. ...................................................... 568/728
(58) Field of Search .......................................... 568/728

(56) References Cited

U.S. PATENT DOCUMENTS

| 4,517,387 A | * | 5/1985 | Matsunaga et al. |
| 5,105,026 A | * | 4/1992 | Powell |
| 5,198,591 A | * | 3/1993 | Kiedik |
| 5,648,561 A |   | 7/1997 | Tan et al. |
| 6,512,148 B1 | * | 1/2003 | Yamamoto |

* cited by examiner

Primary Examiner—Michael L. Shippen
(74) Attorney, Agent, or Firm—Oblon, Spivak, McClelland, Maier & Neustadt, P.C.

(57) ABSTRACT

Provided is a production process for high quality bisphenol A which is reduced in a sulfonic acid-containing heavy matter contained in the product and which is improved in a hue. In an after-treating step for a reaction mixed solution obtained by condensing excess phenol with acetone in the presence of an acid catalyst, a filtering step by a filter is provided at least in one step between a step for dissolving an adduct of bisphenol A and phenol by using a phenol-containing solution and a step for crystallizing and separating the above adduct from this solution.

4 Claims, No Drawings

PROCESS FOR PRODUCING BISPHENOL A

TECHNICAL FIELD

The present invention relates to an improved production process for bisphenol A[2,2-bis(4-hydroxyphenyl)propane], more specifically to a process for efficiently producing bisphenol A having a good hue and a high quality by reducing sulfonic acid-containing heavy matters contained in the product.

BACKGROUND ART

It is known that bisphenol A is an important compound as a raw material for engineering plastics such as a polycarbonate resin and a polyallylate resin and epoxy resins, and demand therefor tends to grow larger and larger in recent years.

This bisphenol A is produced by condensing an excess amount of phenol with acetone in the presence of an acid catalyst and a promoter such as a sulfur compound used in a certain case.

Inorganic mineral acids such as sulfuric acid and hydrochloric acid have so far been used as the acid catalyst used in this reaction. In recent years, cation exchange resins have been paid attentions (British Patents 842209, 849565 and 883391) and used in an industrial scale.

On the other hand, it is known that alkylmercaptans having a substituent or no substituent such as methylmercaptan, ethylmercaptan and thioglycolic acid are effective as the sulfur compound used as the promoter (U.S. Pat. Nos. 2,359,242 and 2,775,620). These mercaptans have functions to elevate a reaction speed and raise a selectivity. For example, in producing bisphenol A, mainly 2-(2-hydroxyphenyl)-2-(4-hydroxyphenyl)propane (o, p'-products) is formed as a reaction by-product, and in addition thereto, trisphenol and polyphenol are formed. In particular, when used as a raw material for a polycarbonate resin and a polyallylate resin, required is high quality bisphenol A which has less contents of these by-products and is not colored. Accordingly, mercaptans are used as a promoter in order to not only elevate the reaction speed but also inhibit the by-products described above from being formed and raise the selectivity.

On the other hand, it is known that an acid has such catalytic function as decomposing bisphenol A into phenol and isopropenylphenol under a high temperature condition. The representative acid includes sulfonic acid used in the production of bisphenol A using a sulfonic acid type cation exchange resin. This sulfonic acid is reacted with iron and bisphenol A at a high temperature of 120° C. or higher to thereby form a black solid sulfonic acid-containing heavy matter (hereinafter referred to as an impurity). The formation of this impurity is accelerated particularly in the presence of water. This impurity has to be effectively removed in order to provide the product bisphenol A with a good hue. Particularly in recent years, bisphenol A having less color and a higher purity than ever is required as a raw material for a polycarbonate resin which increases in demand for optical uses.

It is effective for removing the impurity described above to dispose a filter. Proposed as a technique for providing a filter in the production of bisphenol A are, for example, a process for producing bisphenol A containing only a trace amount of impurity fine particles by providing a sintered metal-made filter in a production process for bisphenol A (Japanese Patent Application Laid-Open No. 180920/1999) and a process for producing bisphenol A in which a fluororesin-made membrane filter is used to reduce impurity fine particles (Japanese Patent Application Laid-Open No. 325184/1996). In these processes, however, the filters are not necessarily disposed in preferred places because of the reasons explained above, and a hue of the product bisphenol A is not necessarily satisfactory.

Further, disclosed is a process for producing bisphenol A having less phenol content by disposing a glass fiber-made filter at least in one point of an outlet in a reaction step, an outlet in a low boiling matter-removing step and an outlet in a heating and melting step (Japanese Patent Application Laid-Open No. 327614/2000). However, if the filter-disposing place is the outlet in the reaction step or the outlet in the low boiling matter-removing step, it is impossible to completely capture sulfonic acid-containing substances, and the sulfonic acid-containing substances which can not be captured are reacted with iron and bisphenol A at a high temperature of 120° C. or higher to form a sulfonic acid-containing heavy matter. This sulfonic acid-containing heavy matter becomes a catalyst for decomposing bisphenol A under a high temperature condition in an after-step to deteriorate a hue of the product bisphenol A. Accordingly, as a melting operation is carried out on a high temperature condition in an outlet of a heating and melting step, a part thereof is considered to be decomposed. Further, a fluid temperature is high, so that a filter-cleaning work is difficult in an aspect of handling, and the heat resistance is required in the specifications of the filter. The matters described above make it less liable to consider that the three points described above are optimum filter-disposing places.

DISCLOSURE OF THE INVENTION

Under such circumstances, an object of the present invention is to provide a process for efficiently producing bisphenol A having a good hue and a high quality by reducing sulfonic acid-containing heavy matters contained in the product.

Intensive researches repeated by the present inventors in order to achieve the object described above have resulted in finding that the object can be achieved by providing a filtering step by a filter at least in one step between a step for dissolving an adduct of bisphenol A and phenol by using a phenol-containing solution and a step for crystallizing and separating the above adduct from this solution in an after step for a reaction mixed solution obtained by condensing phenol with acetone in the presence of an acid catalyst. The present invention has been completed based on such knowledge.

That is, the present invention provides a production process for bisphenol A in which carried out as essential steps after condensing excess phenol with acetone in the presence of an acid catalyst to form bisphenol A are (A) a step for condensing a reaction mixed solution containing substantially no acid catalyst described above, (B) a step for crystallizing and separating an adduct of bisphenol A and phenol from a condensed residual solution obtained in the step (A) described above, (C) a step for dissolving the adduct of bisphenol A and phenol crystallized and separated in the step (B) described above by using a phenol-containing solution, (D) a step for crystallizing and separating the adduct of bisphenol A and phenol from the solution obtained in the step (C) described above and, if necessary, repeating at least once an operation for further dissolving the above adduct by using the phenol-containing solution and then crystallizing and separating it and (E) a step for heating and melting the adduct of bisphenol A and phenol crystallized and separated in the step (D) described above and then distilling phenol off,
wherein a filtering step by a filter is provided at least in one step between the step for dissolving the adduct of bisphenol A and phenol by using the phenol-containing solution in step (C) or step (D) and the step for crystallizing and separating the above adduct from this solution.

BEST MODE FOR PRACTICING THE INVENTION

In the production process for bisphenol A of the present invention, excess phenol is condensed with acetone in the presence of an acid catalyst to form bisphenol A. An acid type ion exchange resin can be used as the acid catalyst described above. This acid type ion exchange resin shall not specifically be restricted, and those which have so far conventionally been used as a catalyst for bisphenol A can be used. In particular, a sulfonic acid type cation exchange resin is suited from the viewpoint of a catalyst activity.

The above sulfonic acid type cation exchange resin shall not specifically be restricted as long as it is a strong acid cation exchange resin having a sulfonic acid group, and it includes, for example, sulfonated styrene-divinylbenzene copolymers, sulfonated cross-linked styrene polymers, phenol formaldehyde-sulfonic acid resins and benzene formaldehyde-sulfonic acid resins. They each may be used alone or in combination of two or more kinds thereof.

In the process of the present invention, mercaptans are usually used as a promoter in combination with the acid type ion exchange resin described above. The mercaptans mean compounds having an SH group in a molecule in a free form, and capable of being used as such compounds are alkylmercaptans, alkylmercaptans having at least one substituent such as a carboxyl group, an amino group and a hydroxyl group, for example, mercaptocarboxylic acid, aminoalkanethiol and mercaptoalcohol. The examples of such mercaptans include alkylmercaptans such as methylmercaptan, ethylmercaptan, n-butylmercaptan and n-octylmercaptan, thiocarboxylic acids such as thioglycolic acid and β-mercaptopropionic acid, aminoalkanethiols such as 2-aminoethanethiol and mercaptoalcohols such as mercaptoethanol. Among them, alkylmercaptans are particularly preferred in terms of an effect as a promoter. These mercaptans may be used alone or in combination of two or more kinds thereof.

These mercaptans can be fixed on the acid type ion exchange resin described above to function as a promoter.

A use amount of the mercaptans described above is usually selected in a range of 0.1 to 20 mole %, preferably 1 to 10 mole % based on acetone of the raw material.

A use proportion of phenol to acetone shall not specifically be restricted, but an amount of unreacted acetone is preferably as small as possible in terms of easiness to refine resulting bisphenol A and the profitability. Accordingly, phenol is advantageously used in excessively more amount than a stoichiometric amount. Usually, phenol is used in an amount of 3 to 30 moles, preferably 5 to 15 moles per mole of acetone. In the production of this bisphenol A, a reaction solvent is not usually needed except the case where the reaction liquid has too high viscosity or the reaction is carried out at such a low temperature that the reaction liquid is coagulated to make the operation difficult.

A condensation reaction of phenol with acetone in the present invention may be either a batch type or a continuous type, and advantageously used is a fixed bed continuous reaction method in which phenol, acetone and mercaptans (in the case where mercaptans are not fixed on an acid type ion exchange resin) are continuously fed into a reaction column filled with an acid type ion exchange resin to react them. In this case, the reaction column may be one or two or more reaction columns may be serially disposed. From an industrial standpoint of view, it is particularly advantageous to employ a fixed bed multistage continuous reaction system in which two or more reaction columns filled with an acid type ion exchange resin are serially connected.

Reaction conditions in this fixed bed continuous reaction system shall be explained.

First, an acetone/phenol mole ratio is selected in a range of usually 1/30 to 1/3, preferably 1/15 to 1/5. If this mole ratio is smaller than 1/30, the reaction speed is likely to be too slow. If it is larger than 1/3, the formation of impurities is increased, and bisphenol A tends to be reduced in a selectivity. On the other hand, if mercaptans are not fixed on an acid type ion exchange resin, a mercaptans/acetone mole ratio is selected in a range of usually 0.1/100 to 20/100, preferably 1/100 to 10/100. If this mole ratio is smaller than 0.1/100, it is likely that an effect of elevating the reaction speed and a selectivity of bisphenol A are not sufficiently revealed, and if it is larger than 20/100, the effect is not observed to be elevated so much in proportion to the amount thereof.

The reaction temperature is selected in a range of usually 40 to 150° C., preferably 60 to 110° C. If the above temperature is lower than 40° C., not only the reaction speed is slow but also the reaction solution has a very high viscosity and is likely to be solidified in a certain case. On the other hand, if it exceeds 150° C., it becomes difficult to control the reaction, and a selectivity of bisphenol A (p, p'-product) is lowered. In addition thereto, the acid type ion exchange resin of the catalyst is decomposed or deteriorated in a certain case. Further, an LHSV (liquid space velocity) of the raw material mixture is selected in a range of usually 0.2 to 30 $hr^{-1}$, preferably 0.5 to 10 $hr^{-1}$.

In the present invention, the reaction mixed solution thus obtained is subjected to after treatment in the state that the acid type ion exchange resin is not substantially contained, that is, after removing the above catalyst by filtering in the case of a batch reaction system and as it is in the case of a fixed bed continuous reaction system.

In the process of the present invention, a step (A) to a step (E) shown below are essential steps in this after treatment, and a filtering step by a filter is provided at least in one step between the step for dissolving the adduct of bisphenol A and phenol described above by using the phenol-containing solution and the step for crystallizing and separating the above adduct from this solution.

Next, the respective steps shall be explained.

Step (A)

This step (A) is a step for condensing the reaction mixed solution described above containing substantially no acid type ion exchange resin. In this condensing step, unreacted acetone, by-produced water and low boiling substances such as alkylmercaptans are usually removed by distillation under reduced pressure using a distilling column.

In general, this distillation under reduced pressure is carried out on the conditions of a pressure of 6.5 to 80 kPa and a temperature of 70 to 180° C. In this case, unreacted phenol boils by azeotropy, and a part thereof is removed to the outside of the system from the head of the distilling column together with the low boiling substances described above. In this distillation, a temperature of a heating source used is preferably controlled to 190° C. or lower in order to prevent bisphenol A from heat decomposition. In general, SUS304, SUS316 and SUS316L are used as a material for the equipments.

Next, a bottom liquid containing bisphenol A and phenol obtained by removing the low boiling substances from the reaction mixture is distilled under reduced pressure to distill phenol off to condense bisphenol A. The condensing conditions thereof shall not specifically be restricted, and the conditions of a temperature of 100 to 170° C. and a pressure of 5 to 70 kPa are usually used. If this temperature is lower than 100° C., high vacuum is required, and if it is higher than 170° C., surplus heat has to be removed in the subsequent crystallizing step. Accordingly, both are not preferred. Bisphenol A contained in the condensed residual liquid has a concentration falling in a range of preferably 20 to 50% by weight, more preferably 20 to 40% by weight. If this concentration is less than 20% by weight, bisphenol A is reduced in a recovering rate. On the other hand, if it exceeds 50% by weight, it is likely to be difficult to transport the slurry after crystallization.

Step (B)

This step (B) is a step for crystallizing and separating a 1:1 adduct (hereinafter referred to as a phenol adduct) of bisphenol A and phenol from the condensed residual liquid obtained in the step (A) described above. In this step, the condensed residual liquid described above is first cooled down to 40 to 70° C. to crystallize the phenol adduct to prepare a slurry. In this case, cooling may be carried out by means of an external heat exchanger or by a vacuum cooling crystallization method in which the condensed residual liquid is cooled down by adding water thereto to make use of vaporization latent heat of water under reduced pressure. In this vacuum cooling crystallization method, 3 to 20% by weight of water is added to the above condensed residual liquid to carry out crystallizing treatment on the conditions of a temperature of 40 to 70° C. and a pressure of 3 to 13 kPa. If an addition amount of water described above is less than 3% by weight, the heat-removing capacity is not sufficiently high. On the other hand, if it exceeds 20% by weight, bisphenol A is increased in dissolution loss. Accordingly, both are not preferred. In such crystallizing operation, a crystallizing temperature of lower than 40° C. is likely to bring about an increase in a viscosity of the crystallization liquid or solidification thereof. On the other hand, if it exceeds 70° C., bisphenol A is increased in dissolution loss. Accordingly, both are not preferred.

Next, the slurry containing the phenol adduct crystallized in the manner described above is separated into the phenol adduct and a crystallization mother liquid containing reaction byproducts by publicly known means such as filtering and centrifugal separation. A part of this crystallization mother liquid may be recycled as it is into the reactor or a part or all thereof may be subjected to alkali decomposition treatment and recovered in the form of phenol and isopropenylphenol. Further, a part or all thereof can be isomerized and recycled to the crystallization raw material.

Step (C)

This step (C) is a step for dissolving the phenol adduct crystallized and separated in the step (B) described above by using a phenol-containing solution. The phenol-containing solution used in this step shall not specifically be restricted and includes, for example, recovered phenol obtained in the condensing step of the step (A) described above, a washing liquid for the phenol adduct generated in the crystallizing and separating step of the step (B), the mother liquid generated in the present step (C) in the solid-liquid separation of the phenol adduct crystallized and a washing liquid for the above phenol adduct.

In this step, the phenol-containing solution described above is added to the phenol adduct obtained in the step (B), and the mixture is heated at 80 to 110° C. to dissolve the above phenol adduct, whereby prepare is a bisphenol A-containing solution having a bisphenol A concentration preferred for a crystallizing operation in the subsequent step. The bisphenol A-containing solution thus prepared has a low viscosity even at a relatively low temperature and is relatively easy to handle, and it is suited to the solid-liquid separation of the phenol adduct crystallized in the subsequent step which is carried out by means of a filter.

Step (D)

This step (D) is a step for crystallizing and separating the phenol adduct from the bisphenol A-containing solution obtained in the step (C) described above and, if necessary, repeating at least once an operation for further dissolving the above phenol adduct by using the phenol-containing solution and then crystallizing and separating it in order to obtain the product having a high purity. The crystallizing and separating operation of the phenol adduct and the dissolving operation of the phenol adduct by the phenol-containing solution in this step are the same as in the step (B) and the step (C) respectively.

Step (E)

This step (E) is a step for heating and melting the phenol adduct crystallized and separated in the step (D) described above and then distilling phenol off. In this step, the phenol adduct is first heated and molten at 100 to 160° C. to obtain a liquid mixture, and then phenol is distilled off under reduced pressure to recover bisphenol A in a molten state. The distillation under reduced pressure described above is usually carried out on the conditions falling in a range of a pressure of 1 to 11 kPa and a temperature of 150 to 190° C. Residual phenol can be removed by steam stripping.

Bisphenol A thus obtained which stays in a molten state is turned into droplets by means of a granulating apparatus such as a spray dryer, and they are cooled and solidified to obtain a product. The above droplets are formed by atomizing or spraying and cooled by nitrogen or air.

The production process for bisphenol A of the present invention is characterized by that a filtering step by a filter is provided at least in one step between the step for dissolving the phenol adduct by using the phenol-containing solution and the step for crystallizing and separating the above phenol adduct from this solution in the steps (A) to (E).

That is, when a crystallizing and separating—dissolving—crystallizing and separating operation is further carried out at least once between the step (C) and the step (D) described above or in the above step (D), at least one filtering step by a filter is provided between this dissolving operation and the crystallizing and separating operation. Thus, filtering of the bisphenol A-containing solution by a filter makes it possible to remove impurities contained in the above solution and prevent bisphenol A from being decomposed under a high temperature condition in the after step. As a result thereof, a colored substance is inhibited from being formed, and the product bisphenol A improved in a hue is obtained.

In this case, a material for the filter used shall not specifically be restricted, and a glass fiber filter usually used is easy to handle and suited. The filtering accuracy of the filter used (maximum diameter of the impurity capable to pass the filter element) is generally 20 $\mu$m or less, preferably 10 $\mu$m or less, though it is different according to the grain size and the content of the impurity. When glass filter is used, the pressure drop of the initial filter element is about 0.03 to 0.04 MPa. This pressure drop is increased by blocking and the filter element is changed to new one when the pressure drop of the filter element become about 0.10 to 0.20 MPa.

In the production process for bisphenol A, The sulfonic acid from the cation exchange resin is reacted with bisphenol A and iron from reactor and the like to form a black solid sulfonic acid-containing heavy matter as an impurity. This impurity is formed in many cases in a low boiling matter-removing step and a condensing step which are provided as after steps for treating a reaction solution after condensing phenol with acetone, and therefore it is important to dispose a filter in a step after the impurity is formed. However, if it is disposed in a step where a fluid temperature after the impurity is formed is high, the decomposition of bisphenol A is caused before removing the impurity, and therefore it is not preferred. Further, the fluid has a high melting point and is liable to be solidified, so that complicated operation is required in an aspect of handling. Accordingly, it is important to dispose a filter in a step where a fluid temperature is low. Further, removing the impurity as quickly as possible makes it possible to prevent the impurity from diffusing into the production process to elevate a hue of the product bisphenol A.

Next, the present invention shall be explained in further details with reference to examples, but the present invention shall by no means be restricted by these examples.

EXAMPLE 1

Phenol and acetone in a mole ratio 10:1 were continuously passed through a fixed bed reaction column charged with a cation exchange resin ([Diaion SK103H], manufactured by Mitsubishi Chemical Co., Ltd.) at an LHSV of 3 $hr^{-1}$ together with ethylmercaptan to react them at 75° C.

Acetone, water and ethylmercaptan were removed from the resulting reaction solution by distillation under reduced pressure on the conditions of a column bottom temperature of 170° C. and a pressure of 67 kPa. Then, it was further distilled under reduced pressure on the conditions of a temperature of 130° C. and a pressure of 14 kPa to distil phenol off and condensed until the bisphenol A concentration reached 40% by weight to obtain a phenol-bisphenol A solution.

Next, water was added to this phenol-bisphenol A solution having a bisphenol A concentration of 40% by weight, and the solution was cooled down to 50° C. under reduced pressure and maintained, whereby a bisphenol A.phenol adduct was crystallized to obtain a slurry solution.

Then, the slurry solution thus obtained was subjected to solid-liquid separation to thereby obtain a bisphenol A.phenol adduct. Phenol was added to this adduct, and the solution was heated at 90° C. to prepare a solution containing 60% by weight of phenol and 40% by weight of bisphenol A. Next, this solution was filtered through a glass fiber filter (glass fiber filter, filtering accuracy: 10 μm, manufactured by Lokitechno Co., Ltd.), and then the same vacuum cooling crystallization and solid-liquid separation were carried out to obtain a bisphenol A.phenol adduct. Then, this adduct was washed with refined phenol to obtain a bisphenol A.phenol adduct crystal. This adduct crystal was heated and molten at 130° C. and then subjected to dephenol to obtain bisphenol A.

Bisphenol A described above was heated at 220° C. for 40 minutes under air environment to visually evaluate the hue using an APHA standard color, and as a result thereof, the hue was APHA 15.

COMPARATIVE EXAMPLE 1

Bisphenol A was obtained in the same manner as in Example 1, except that in Example 1, the reaction solution was filtered through the glass fiber filter (described above) and the solution obtained by adding phenol to the bisphenol A.phenol adduct crystallized and separated to dissolve the above adduct was not filtered through the filter. This bisphenol A had a hue of APHA 40.

COMPARATIVE EXAMPLE 2

Bisphenol A was obtained in the same manner as in Example 1, except that in Example 1, added was filtering of the phenol.bisphenol A solution (bisphenol A concentration: 40% by weight) obtained by condensation through the glass fiber filter (described above) and omitted was filtering of the solution obtained by adding phenol to the bisphenol A.phenol adduct crystallized and separated to dissolve the above adduct through the filter. This bisphenol A had a hue of APHA 30.

INDUSTRIAL APPLICABILITY

According to the present invention, capable of being efficiently produced is high quality bisphenol A which is reduced in a sulfonic acid-containing heavy matter contained in the product and which is improved in a hue.

What is claimed is:

1. A production process for bisphenol A in which carried out as essential steps after condensing excess phenol with acetone in the presence of an acid catalyst to form bisphenol A are (A) a step for condensing a reaction mixed solution containing substantially no acid catalyst described above, (B) a step for crystallizing and separating an adduct of bisphenol A and phenol from a condensed residual solution obtained in the step (A) described above, (C) a step for dissolving the adduct of bisphenol A and phenol crystallized and separated in the step (B) described above by using a phenol-containing solution, (D) a step for crystallizing and separating the adduct of bisphenol A and phenol from the solution obtained in the step (C) described above and, if necessary, repeating at least once an operation for further dissolving the above adduct by using the phenol-containing solution and then crystallizing and separating it and (E) a step for heating and melting the adduct of bisphenol A and phenol crystallized and separated in the step (D) described above and then distilling phenol off, wherein a filtering step by a filter is provided at least in one step between the step for dissolving the adduct of bisphenol A and phenol by using the phenol-containing solution in step (C) or step (D) and the step for crystallizing and separating the above adduct from this solution.

2. The production process for bisphenol A as described in claim 1, wherein the filter is a glass fiber filter.

3. The production process for bisphenol A as described in claim 1, wherein the acid catalyst is a sulfonic acid type cation exchange resin.

4. The production process for bisphenol A as described in claim 2, wherein the acid catalyst is a sulfonic acid type cation exchange resin.

* * * * *